US010434306B2

United States Patent
Goode et al.

(10) Patent No.: US 10,434,306 B2
(45) Date of Patent: *Oct. 8, 2019

(54) ENHANCED OUTER SHEATH FOR EXTRACTION DEVICE

(71) Applicant: Cook Medical Technologies LLC, Bloomington, IN (US)

(72) Inventors: Louis B. Goode, Cranberry Township, PA (US); Chun Kee Lui, Apollo, PA (US); Michael Wayne Emmert, Apollo, PA (US); Robert Booker, Vandergrift, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 154 days.

This patent is subject to a terminal disclaimer.

(21) Appl. No.: 15/419,210

(22) Filed: Jan. 30, 2017

(65) Prior Publication Data

US 2017/0136230 A1    May 18, 2017

Related U.S. Application Data

(63) Continuation of application No. 13/975,737, filed on Aug. 26, 2013, now Pat. No. 9,586,041.

(51) Int. Cl.
*A61N 1/05*  (2006.01)

(52) U.S. Cl.
CPC ............. *A61N 1/057* (2013.01); *A61N 1/056* (2013.01); *A61N 1/059* (2013.01); *A61N 2001/0578* (2013.01)

(58) Field of Classification Search
CPC . A61B 17/0401; A61B 17/0487; A61B 17/10; A61B 17/128; A61B 17/3468; A61B 2017/0411; A61B 2017/049; A61N 1/05
See application file for complete search history.

(56) References Cited

U.S. PATENT DOCUMENTS 2,261,230 A   11/1941  Cox et al.
3,132,549 A    5/1964  Lee
(Continued)

FOREIGN PATENT DOCUMENTS

EP     0 807 412 A1   11/1997
EP     1 820 458 A1    8/2007
WO   WO 2006/113438 A2  10/2006

OTHER PUBLICATIONS

Albee, F., "Bone Surgery with Machine Tools," Scientific American, Apr. 1936, pp. 178-181.

(Continued)

*Primary Examiner* — Todd J Scherbel
(74) *Attorney, Agent, or Firm* — Brinks Gilson & Lione

(57) ABSTRACT

A device for extracting an elongated implanted structure from an obstruction within a vessel of a patient includes an inner sheath assembly and an outer sheath assembly. The inner sheath assembly includes an inner sheath and a tip, each having a passageway therethrough for receiving the implanted structure. The tip is configured for cutting and/or disrupting the implanted structure from the obstruction. The outer sheath assembly includes an outer sheath and a tip, each having a passageway therethrough for receiving the inner sheath assembly. The outer surface of this tip includes a plurality of raised elements circumferentially disposed therealong. The raised elements are configured for stabilizing the tissue of the vessel as the device is advanced through the vessel.

20 Claims, 11 Drawing Sheets

(56) References Cited

U.S. PATENT DOCUMENTS

| | | |
|---|---|---|
| 3,519,046 A | 7/1970 | Pierce |
| 3,756,090 A | 9/1973 | Mella et al. |
| 4,030,503 A | 6/1977 | Clark, III |
| 4,084,594 A | 4/1978 | Mosior |
| 4,174,858 A | 11/1979 | Brooks |
| 4,576,162 A | 3/1986 | McCorkle |
| 4,643,190 A | 2/1987 | Heimberger |
| 4,943,289 A | 7/1990 | Goode et al. |
| 4,988,347 A | 1/1991 | Goode et al. |
| 5,011,482 A | 4/1991 | Goode et al. |
| 5,013,310 A | 5/1991 | Goode et al. |
| 5,052,402 A | 10/1991 | Bencini et al. |
| 5,092,848 A | 3/1992 | deCiutiis |
| 5,122,134 A | 6/1992 | Borzone et al. |
| 5,207,683 A | 5/1993 | Goode et al. |
| 5,363,726 A | 11/1994 | Smith |
| 5,423,806 A | 6/1995 | Dale et al. |
| 5,447,534 A | 9/1995 | Jammet |
| 5,507,751 A | 4/1996 | Goode et al. |
| 5,591,187 A | 1/1997 | Dekel |
| 5,632,749 A | 5/1997 | Goode et al. |
| 5,651,781 A | 7/1997 | Grace |
| 5,697,936 A | 12/1997 | Shipko et al. |
| 5,769,858 A | 6/1998 | Pearson et al. |
| 5,814,044 A | 9/1998 | Hooven |
| 5,830,221 A | 11/1998 | Stein et al. |
| 5,830,231 A | 11/1998 | Geiges, Jr. |
| 5,913,857 A | 6/1999 | Ritchart et al. |
| 5,980,515 A | 11/1999 | Tu |
| 5,980,545 A | 11/1999 | Pacala et al. |
| 5,984,939 A | 11/1999 | Yoon |
| 5,993,467 A | 11/1999 | Yoon |
| 6,010,476 A | 1/2000 | Saadat |
| 6,099,537 A | 8/2000 | Sugai et al. |
| 6,135,947 A | 10/2000 | Watanabe et al. |
| 6,136,005 A | 10/2000 | Goode et al. |
| 6,190,353 B1 | 2/2001 | Makower et al. |
| 6,283,511 B1 | 9/2001 | Kamp |
| 6,332,886 B1 | 12/2001 | Green et al. |
| 6,419,974 B1 | 7/2002 | Silva et al. |
| 6,503,261 B1 | 1/2003 | Bruneau et al. |
| 6,656,195 B2 | 12/2003 | Peters et al. |
| 6,687,548 B2 | 2/2004 | Goode |
| 6,712,826 B2 | 3/2004 | Lui |
| 6,712,855 B2 | 3/2004 | Martin et al. |
| 6,783,533 B2 | 8/2004 | Green et al. |
| 9,586,041 B2 * | 3/2017 | Goode ............... A61N 1/059 |
| 2002/0143358 A1 | 10/2002 | Domingo et al. |
| 2002/0172923 A1 | 11/2002 | Strong et al. |
| 2003/0040787 A1 | 2/2003 | Flynn et al. |
| 2004/0143287 A1 | 7/2004 | Konstantino et al. |
| 2004/0260336 A1 | 12/2004 | Braun |
| 2005/0107816 A1 | 5/2005 | Pingleton et al. |
| 2005/0273125 A1 | 12/2005 | Opie |
| 2006/0235431 A1 | 10/2006 | Goode et al. |
| 2006/0253179 A1 | 11/2006 | Goode et al. |
| 2008/0071341 A1 | 3/2008 | Goode et al. |
| 2008/0071342 A1 | 3/2008 | Goode et al. |
| 2008/0154293 A1 | 6/2008 | Taylor |
| 2012/0323252 A1 | 12/2012 | Booker |

OTHER PUBLICATIONS

Extended Search Report for Corresponding European Patent Application No. 14 18 188, dated Nov. 4, 2014, 7p.

* cited by examiner

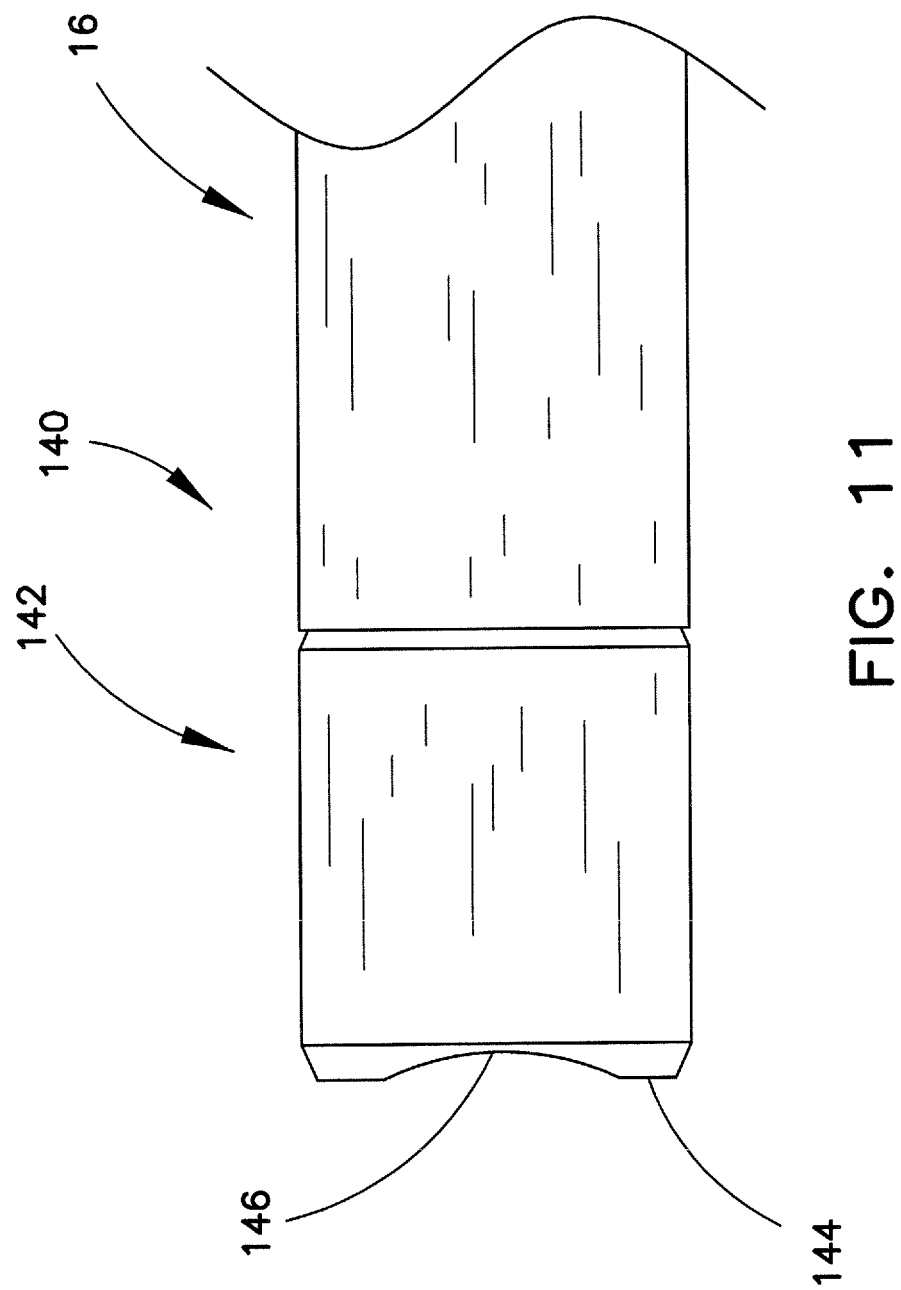

ENHANCED OUTER SHEATH FOR EXTRACTION DEVICE

CROSS-REFERENCE TO RELATED APPLICATIONS

This application claims priority to U.S. Non-Provisional application Ser. No. 13/975,737, filed Aug. 26, 2013, and titled "Enhanced Outer Sheath For Extraction Device", the contents of which are incorporated herein by reference.

BACKGROUND

1. Technical Field

This invention relates generally to a device for use in separating an implanted elongated structure from encapsulating tissue in the body of a patient. More particularly, the invention relates to an extraction device having an enhanced outer sheath for separating a cardiac lead from encapsulating biological tissue.

2. Background Information

A variety of medical treatments and surgical methods entail implanting an elongated structure in the body of a patient. Examples of such elongated structures include cardiac leads (such as pacemaker leads and defibrillator leads), medical prostheses (such as stents), as well as a variety of other devices. Over time, it can become necessary or desirable to remove the implanted elongated structure from the body of the patient. However, if the elongated structure has been implanted for an extended period of time, encapsulating biological tissue may have grown around the elongated structure, making it difficult to remove the structure from the encapsulating tissue.

A heart pacemaker is typically implanted in a subcutaneous tissue pocket in the chest wall of a patient. A pacemaker lead extends from the pacemaker through a vein into a chamber of the patient's heart. The pacemaker lead commonly includes a conductor, such as an electrical wire coil, for conducting electrical signals (such as stimulating and/or sensing signals) between the pacemaker and the heart. Leads for defibrillators are generally similar to pacemaker leads, and are positioned about the heart. Defibrillator leads may be affixed either internally or externally of the heart.

While cardiac leads typically have a useful life of many years, over time such leads may become encapsulated by fibrotic tissue against the heart itself or the wall of the vein, against other surrounding tissue, or even against other cardiac leads in the vein. Encapsulation is especially encountered in areas where the velocity of the flow of blood is low. The fibrotic tissue can be very tough, which makes it difficult to remove the lead from the area of the heart without causing trauma to the area. When small diameter veins through which a cardiac lead passes become occluded with fibrotic tissue, separation of the lead from the vein can cause damage to the vein, including the possible dissection or perforation of the vein. In such cases, separation of the lead from the vein is usually not possible without restricting or containing movement of the lead, i.e., fixing the lead in position with respect to the patient, in particular, with respect to the patient's vein.

To avoid this and other possible complications, some useless or otherwise inoperable cardiac leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are many other reasons why removal of an inoperable lead may be desirable. For example, if there are too many leads positioned in a vein, the vein can be obstructed to the extent that fluid flow through the vein is compromised. In addition, multiple leads can be incompatible with one another, thereby interfering with the pacing or defibrillating function. An inoperable lead can migrate during introduction of an adjacent second lead, and mechanically induce ventricular arrhythmia. Other potentially life-threatening complications can require the removal of the lead as well. For example, removal of an infected cardiac lead may be desirable so as to avoid conditions such as septicemia or endocarditis. Finally, such removable may be desirable so that the space occupied by the inoperable lead in the vein could be better utilized, e.g., by the presence of a new lead.

Surgical removal of a heart lead in such circumstances may require open heart surgery. However, open heart surgery is accompanied by significant risk and cost to the patient, as well as a potential for unintended complications. A variety of methods and apparatuses have been devised as alternatives to open heart surgery for heart lead removal. Several of these methods and apparatuses are described in related patents and publications, such as U.S. Pat. No. 5,697,936, titled "Device for Removing an Elongated Structure Implanted in Biological Tissue"; U.S. Pat. No. 5,507,751, titled "Locally Flexible Dilator Sheath"; U.S. Pat. No. 5,632,749, titled "Apparatus for Removing an Elongated Structure Implanted in Biological Tissue"; U.S. Pat. No. 5,207,683, titled "Apparatus for Removing an Elongated Structure Implanted in Biological Tissue"; U.S. Pat. No. 4,943,289, titled "Apparatus for Removing an Elongated Structure Implanted in Biological Tissue"; U.S. Pat. No. 5,011,482, titled "Apparatus for Removing an Elongated Structure Implanted in Biological Tissue"; U.S. Pat. No. 5,013,310, titled "Method and Apparatus for Removing an Implanted Pacemaker Lead"; U.S. Pat. No. 4,988,347, titled "Method and Apparatus for Separating a Coiled Structure from Biological Tissue"; U.S. Pat. No. 5,423,806, titled "Laser Extractor for an Implanted Object"; U.S. Pat. No. 6,419,674, titled "Radio Frequency Dilator Sheath", U.S. Pat. Nos. 6,687,548 and 6,712,826, each titled "Apparatus for Removing an Elongated Structure Implanted in Biological Tissue"; U.S. Patent Publ. No. 2006/0235431, titled "Lead Extraction Device" U.S. Patent Publ. No. 2006/0253179, titled "Tip for Lead Extraction Device"; U.S. Patent Publ. No. 2008/0071341, titled "Tip for Lead Extraction Device"; U.S. Patent Publ. No. 2008/0071342, titled "Vessel Entry Device"; and U.S. Patent Publ. No. 2012/0323252, among others. Each of the aforementioned patents and patent publications is incorporated by reference as if fully set forth herein.

Many of the aforementioned patents and patent publications describe manual, or mechanical, devices that are used for removing an implanted structure, such as a cardiac lead. Others describe non-mechanical techniques, such as laser extraction and radio frequency extraction. Although the prior art devices have been found to be reasonably effective in many situations, physicians continue to encounter particularly challenging situations in which existing extraction devices may not provide satisfactory or consistent results. Due to the multiplicity of factors that may contribute to the difficulty in extracting an implanted lead, a technique that may be effective in one instance may not provide similarly successful results in another instance.

For example, laser and radio frequency devices normally utilize metallic sheaths. Such sheaths typically provide a good deal of strength to enable the sheath to cut through fibrous growths. However, some growths are resistant to metallic sheaths. In addition, these sheaths may lack the flexibility desired to maneuver tortuous pathways. Laser and radio frequency systems can also be expensive, particularly when compared to mechanical devices. Further, many facilities lack the equipment necessary to carry out these techniques.

Lead extraction devices may be provided with a single rotating flexible sheath, or dual telescoping flexible sheaths, for tracking over the cardiac lead. Such sheaths are generally formed from a polymer, and have the flexibility to enable the sheath to traverse tortuous pathways in the vessel. However, such sheaths may lack sufficient strength to cut through particularly tough tissue growth and calcification around the implanted lead.

As described in many of the incorporated-by-reference documents cited above, many such devices are provided with a tip at the distal end of the innermost sheath. For example, the prior art tip shown in FIG. 6 may include a generally helical or like structure protruding radially from the outer surface of the tip. Among other things, the radial protrusion may enhance the ability of the tip to core or otherwise non-cuttingly disrupt the encapsulating tissue from the lead as the rotating sheath and tip advance through the vessel. Another example of a prior art tip is shown in FIG. 7. This tip has a generally flat leading face, and a plurality of sides (such as ten) extending circumferentially around the leading end of the tip. Each of the sides has two ends, and an inwardly directed radiused portion between said ends. The presence of the radius, along and the lack of radially outwardly protruding structure, provides a lower profile and a less aggressive leading face when compared to the tip of FIG. 6. This structure may be successful in disrupting some obstructions that have been found problematic with a tip such as that shown in FIG. 6.

In these dual sheath extraction devices, the outer sheath typically functions as a conduit to facilitate advancement of the inner sheath, and does not otherwise provide a cutting or disrupting action to the device in the nature of the innermost tipped sheath. Although the innermost tipped sheath has been found to be reasonably effective in many cases for freeing an implanted lead from encapsulating biological tissue, particularly difficult cases may arise in which the tissue is resistant to this inner sheath and tip.

It would be desirable to provide a device and tip structure that is effective for removing implanted medical structures from a vessel, that is easy to operate, and that is versatile enough to overcome many of the obstacles that may be encountered in such operations with existing dual sheath extraction devices. It is further desired to provide an extraction device in which the outer sheath is provided with a tip that enables the sheath to assist the inner sheath in advancing through an obstruction surrounding an implanted lead.

BRIEF SUMMARY

The present invention addresses the problems of the prior art extraction devices. In one form thereof, the invention comprises a device for extracting an elongated implanted structure from an obstruction within a vessel of a patient. The device includes an inner sheath assembly comprising an inner sheath and a tip. The inner sheath has a distal end, and has a passageway extending therethrough. The sheath is sufficiently flexible to track over the implanted structure within the vessel. The tip has a proximal portion, a distal portion having an outer surface, and a passageway extending therethrough. The proximal portion is engaged with the sheath distal end such that the respective passageways are aligned to receive the implanted structure therein. An outer sheath assembly comprises an outer sheath and a tip, the outer sheath having a distal end, an outer diameter, and a passageway extending therethrough. The outer sheath is sufficiently flexible to track over the inner sheath assembly. The tip has a proximal portion, a distal portion, and a passageway extending therethrough. The tip proximal portion is engaged with the sheath distal end such that the respective passageways are aligned to receive the inner sheath assembly therein. The tip distal portion is configured in a manner to facilitate a disruption of the implanted structure from the obstruction.

In another form thereof, the invention comprises a device for extracting an elongated implanted structure from an obstruction within a body vessel of a patient. An inner sheath assembly comprises an elongated inner sheath and a tip positioned at a distal end of the inner sheath. Each of the inner sheath and tip have a passageway therethrough for receiving the implanted structure therein. An outer sheath assembly comprises an elongated outer sheath and a tip affixed at a distal end of the outer sheath. Each of the outer sheath and tip have a passageway therethrough for receiving the inner sheath assembly. A distal portion of the tip includes a plurality of raised elements circumferentially disposed along an outer surface thereof. The raised elements are configured for stabilizing tissue of the vessel during an advancement of the inner sheath assembly through the vessel. A handle is configured for engagement with a proximal end of the elongated inner sheath. The handle includes an actuator and a drive mechanism responsive to the actuator. The drive mechanism is operable to translate input of the actuator into at least one of rotational and axial movement of the inner sheath assembly in the vessel.

BRIEF DESCRIPTION OF THE DRAWINGS

FIG. 11 is a side view of the distal portion of another example of an outer sheath assembly.

DETAILED DESCRIPTION OF THE DRAWINGS AND THE PRESENTLY PREFERRED EMBODIMENTS

Figure 1:
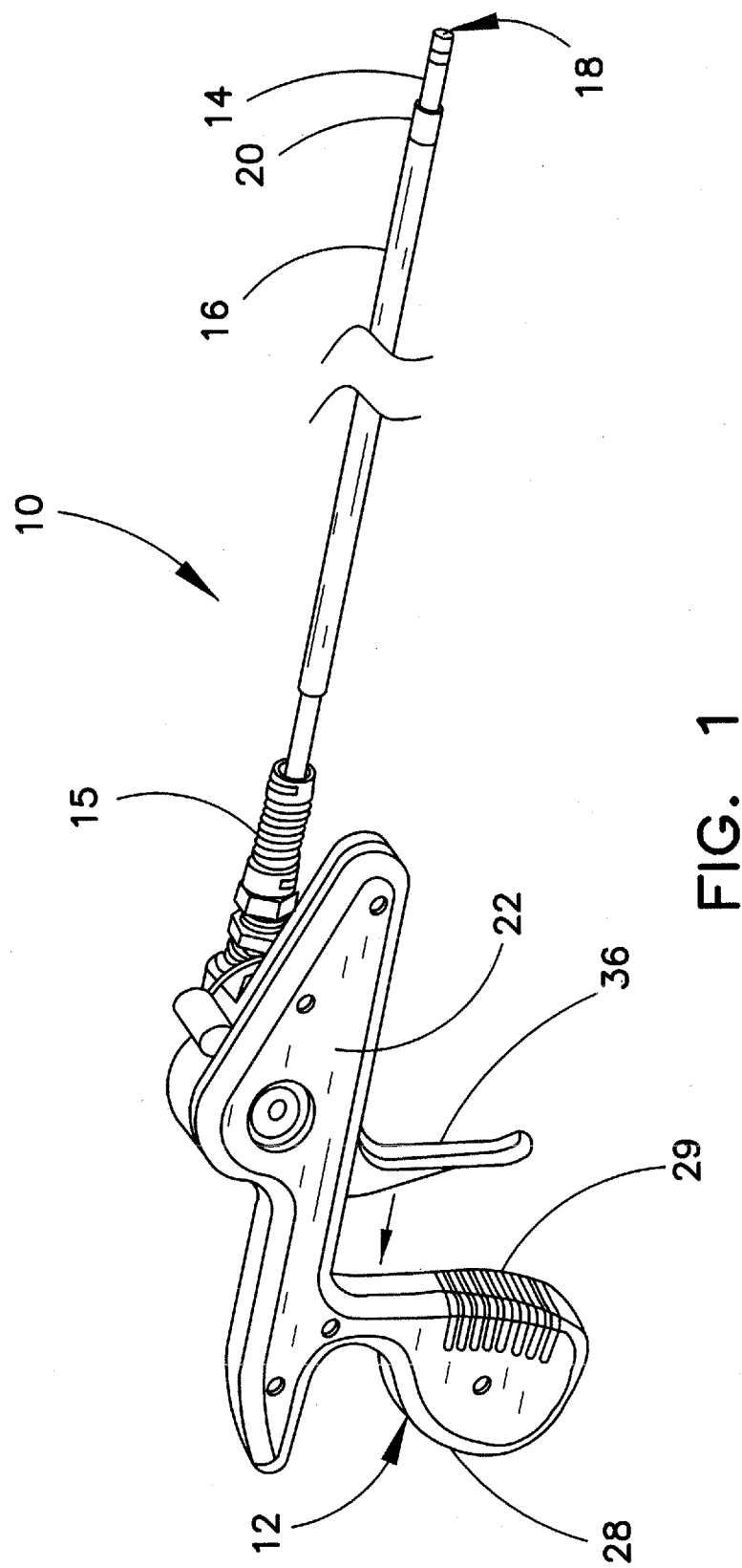
FIG. 1 is a perspective view of an embodiment of a lead extraction device of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the device, as well as the axial ends of various component features of the device. The term "proximal" is used in its conventional sense to refer to the end of the device (or component thereof) that is closest to the operator during use of the device. The term "distal" is used in its conventional sense to refer to the end of the device (or component) that is at the greatest distance from the operator, and/or that is initially inserted into the patient.

The implanted elongated structure targeted for removal may comprise a cardiac lead. A cardiac lead, as the term is used herein, refers to a lead that is used in connection with a heart-related device. Non-limiting examples of cardiac leads that may be extracted by the inventive device include pacemaker leads, defibrillator leads, coronary sinus leads, and left ventricular pacing leads. When the device is used to remove a cardiac pacemaker lead, the distal end of the cardiac lead will normally be located within the vascular system of the patient, and in particular, within a chamber of the patient's heart (such as in an atrium or ventricle of the heart). When the implanted elongated structure is a defibrillator lead, the distal end of the structure may be located either in or about the heart of the patient. The distal ends of other types of implanted elongated structures targeted for removal may not necessarily be near the heart.

In addition to cardiac leads, the invention may also be used in the removal of other elongated structures or leads, such as neurological pacing and stimulation leads. A non-limiting list of still other structures that can be removed by the inventive device includes implanted catheters, sheaths, cannulae, prostheses, and the like. For convenience the following discussion will refer to the removal of a cardiac lead, such as a pacemaker or a defibrillator lead. However it should be understood that this is not intended to be a limitation on the scope of the invention, and that the device may be suitable for removal of other elongated structures, such as the structures referred to above.

Typically, a cardiac lead comprises an inner core, comprising a cable or a coil, surrounded by a layer of insulating material. Some cardiac leads have a lumen extending therethrough, while others (i.e., "lumenless" leads) do not. The extraction devices of the present invention are useful for extracting implanted leads having a lumen, as well as lumenless leads. When an inventive device is to be used for removal of a cardiac lead, those skilled in the art will appreciate that the lead should initially be severed from the control device, such as the pacemaker or defibrillator, prior to any attempts to remove the lead. Since the control device will normally have a much larger diameter than the remainder of the lead, only an unreasonably large dilator sheath could fit over the control device.

FIG. 1 is a perspective view of one embodiment of a lead extraction device 10 for use in separating an elongated structure, such as a cardiac electrical lead, from encapsulating biological tissue. When a cardiac lead is implanted in a vessel, all or a portion of the elongated structure of the lead may become encapsulated over time by fibrotic biological tissue that grows against the wall of the vessel or surrounding tissue. The inventive lead extraction device 10 is particularly useful for removing the encapsulated cardiac lead from the vein of a patient. In the embodiment shown, lead extraction device 10 comprises a handle 12, and coaxial inner and outer sheaths 14, 16 extending distally from handle 12. Tip 18 is engaged at the distal end of inner sheath 14, and tip 20 is engaged at the distal end of outer sheath 16. As shown in the figure, an optional strain relief 15 may be provided at the proximal end of inner sheath 14 to inhibit kinking.

Although the presence of handle 12 is preferred in lead extraction device 10, this feature is optional and need not be included in all instances. Many users may find the handle to be convenient in providing rotary action to inner sheath 14. However, other users may prefer to manually rotate and/or advance the respective sheaths into the vessel. Therefore, lead extraction device 10 may, or may not, include a handle such as that shown in the figures.

Outer sheath 16 is typically free floating in the device, or in other words, is not affixed to other portions of the device. In the non-limiting example shown, outer sheath 16 extends a majority of the length of the inner sheath 14, but is typically shorter at each axial end. The outer sheath will typically have a free proximal end for grasping by the physician. The physician may manually manipulate the lead end as desired, e.g., for inhibiting other objects, such as other indwelling devices (other pacing leads, etc.), from interfering with the inner sheath as the inner sheath rotates. The outer sheath can also aid in dilating the vessel entry site to allow for smoother entry and reentry of subsequent extraction devices. In addition, if the primary lead anchoring location is at the vessel entry site, the lead may readily slide out once the device gains vessel access. In this instance, the outer sheath functions as a conduit in allowing the lead to be drawn past tortuous regions (such as the tight clavicular region), and out of the body.

Figure 2:
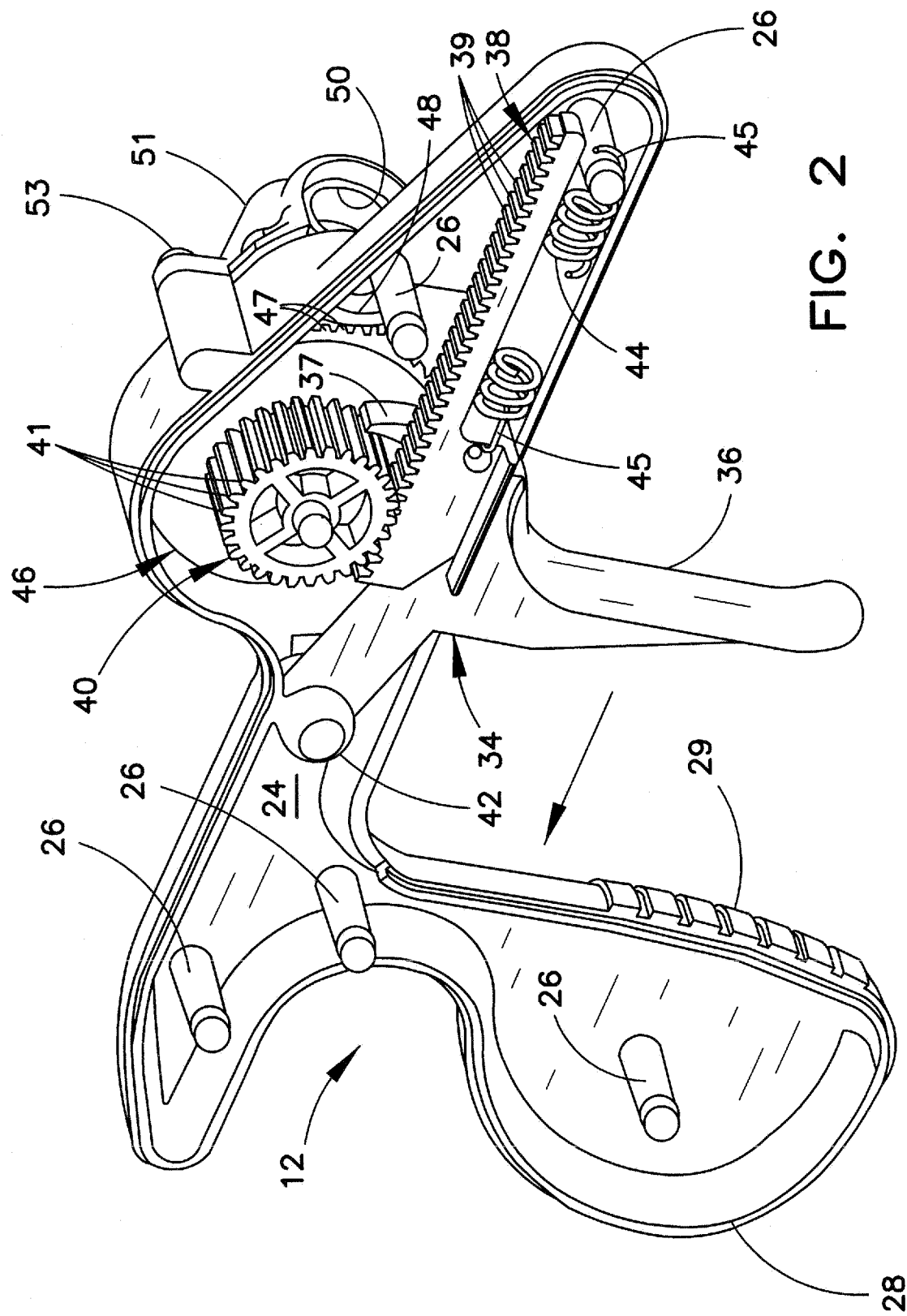
FIG. 2 is a perspective view of the handle of the lead extraction device of FIG. 1, with a portion of the outer wall removed to illustrate the inner components of the handle.

In the illustrated example, optional handle 12 includes opposing handle walls 22, 24. FIG. 2 is a perspective view of handle 12 wherein handle outer wall 22 has been removed to provide visualization of the internal workings of this handle. Handle walls 22, 24 are connected via a snap fit or other conventional mechanism. In the example shown, handle wall 24 includes a plurality of transverse pegs 26 that are received in corresponding receptacles (not shown) in handle wall 22. Handle 12 may be provided with an ergonomically shaped grip 28, as shown in the figures. If desired, ergonomic grip 28 may also include a plurality of ribs 29 spaced along a hand-engaging surface of grip 28.

When present, handle 12 preferably includes a translation mechanism 34. Translation mechanism 34 utilizes, e.g., a rack and gear structure to translate linear motion generated upon pull of an actuator, such as trigger 36, into rotational motion of inner sheath 14. Translation mechanism 34 includes a rack 38 having a plurality of teeth 39 as shown. Rack 38 is engaged with trigger 36, such that upon the operator pulling trigger 36 in the proximal direction (as indicated by the arrow in FIG. 2), rack 38 likewise is urged linearly in the proximal direction.

An external spur gear 40, having a plurality of teeth 41, is aligned with rack 38 such that spur gear teeth 41 mesh with rack teeth 39. Linear movement of rack teeth 29 causes spur gear 40, and thus teeth 41, to rotate in the direction shown. A pawl 37 may be provided to inhibit undesired (counter-clockwise) rotation of the spur gear. If desired, pawl 37 may also be configured to create ratcheting action upon movement of rack 38 and spur gear 40, and to provide an audible confirmation of the rotation of the spur gear. A stabilizing arm 42 extending in a proximal direction from rack 38 may be provided to maintain proper orientation of rack 38 in handle 12, and to ensure smooth movement of the trigger without bending or flexing when pulled under a load. Preferably, a spring 44 is affixed at one end to rack 38 and at the other end to housing wall peg 26 (distal of rack 38), for urging trigger 36 back to the position shown in FIG. 2 upon relaxation of the tension resulting from the trigger pull by the operator. Spring 44 may be retained in handle 12 by any conventional means, such as hooks 45.

Spur gear 40 is affixed to large bevel gear 46, in a manner such that rotation of spur gear 40 causes a corresponding rotation of large bevel gear 46. Large bevel gear 46 includes a plurality of teeth 47 on a side of large bevel gear 46 opposite spur gear 40. A small bevel gear 48 is rotationally aligned with large bevel gear 46 in conventional fashion, such that large bevel gear teeth 47 mesh with small bevel gear teeth (not shown). The large and small bevel gears are aligned in conventional fashion for such bevel gears, e.g., at an angle of about 90 degrees. As a result, the direction of rotation is translated via said gears along the 90 degree angle.

A hub 50 is affixed to small bevel gear 48 for rotation in accordance with the rotation of the small bevel gear. Hub 50 is sized and shaped to securely receive a proximal end of inner sheath 14, by conventional means such as adhesion, friction and/or threading. Sheath 14 is preferably engaged with the hub 50 in a manner such that it may be selectively affixed to, or removed from, the hub. Further description of the handle is provided in incorporated-by-reference U.S. Patent Publication 2006/0253179.

Figure 3:
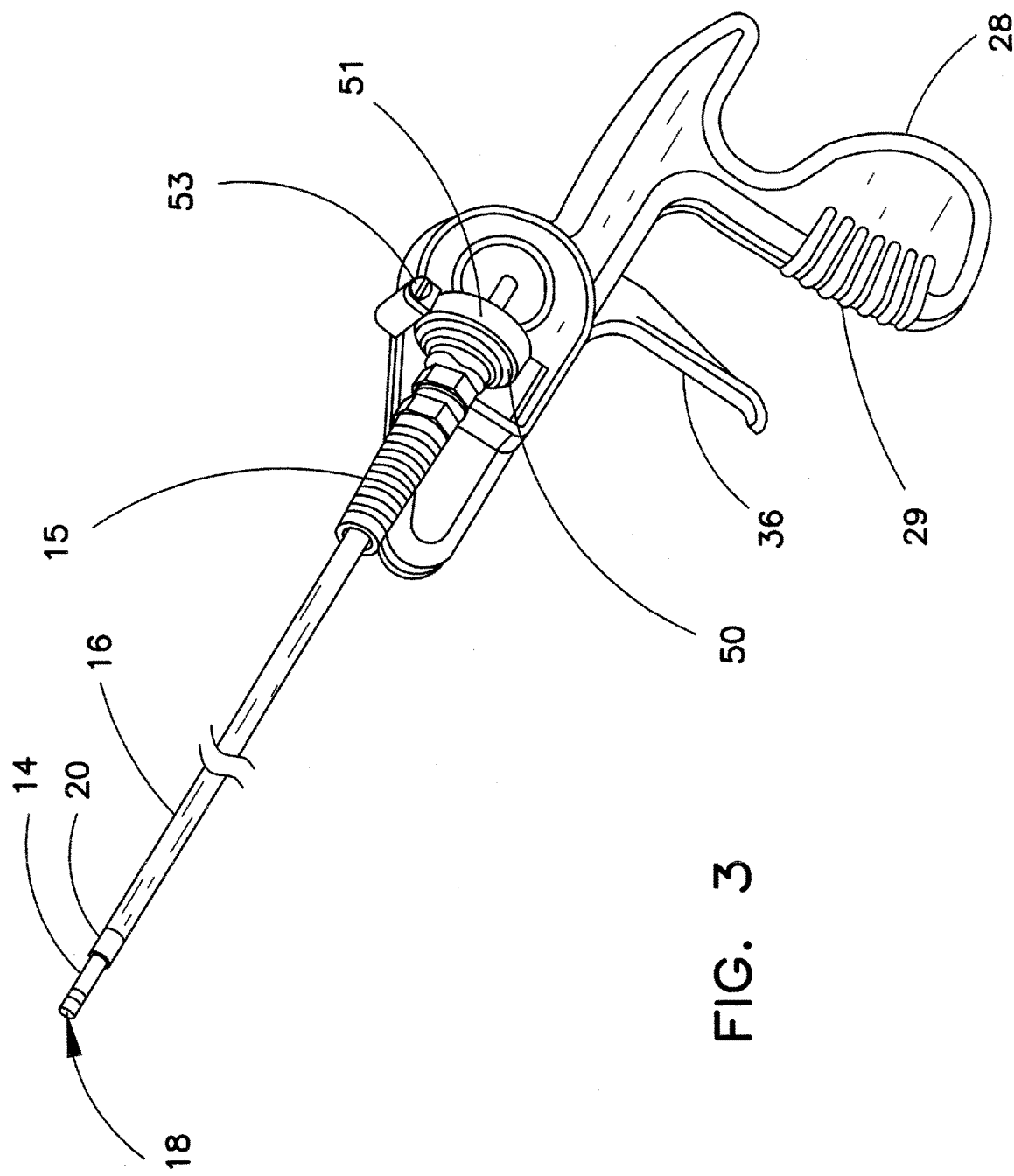
FIG. 3 is a side view of the opposite side of the lead extraction device shown in FIG. 1.
Figure 4:
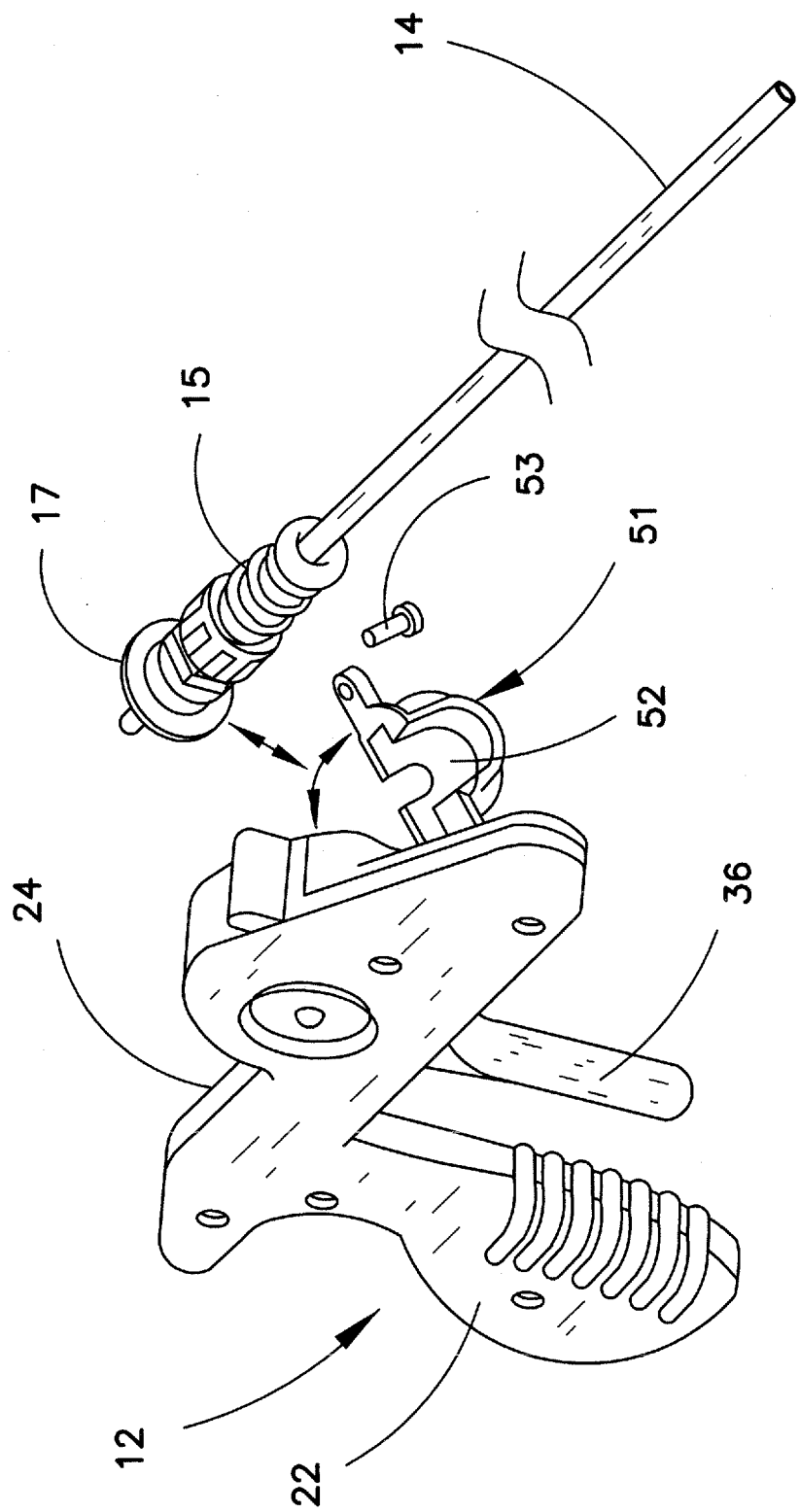
FIG. 4 is a view showing the handle and inner sheath of the lead extraction device prior to assembly.

FIG. 4 illustrates one preferred manner in which inner sheath 14 is removably affixed to device 10. Handle wall 24 includes a pivotable wall portion 51 that may be pivoted to the open position as shown in the figure. In this example, inner sheath 14 is provided with a flange 17 at the proximal end of the sheath, to seat the inner sheath in the hub. When the sheath is affixed in hub 50, flange 17 is snugly received against a surface 52 of pivotable portion 51. When portion 51 is pivoted into the closed position, a conventional latching mechanism, such as a screw 53 is provided to maintain pivotable portion 51 in the closed position shown in FIG. 3, thereby retaining inner sheath 14 in handle 12. Those skilled in the art will appreciate that there are numerous other ways in which the inner sheath may be held in the device, and that the particular removable affixation mechanism described herein is not crucial to the invention. Following the engagement of inner sheath as described, outer sheath 16 may simply be slid over the distal end of inner sheath 14 (FIG. 1).

Thus, inner sheath 14 may be selectively engaged with, and disengaged from, handle 12. In this manner, inner and outer sheaths 14, 16 may simply be disengaged or otherwise removed following a lead extraction procedure, and replaced with other similar sheaths for use in a subsequent procedure. Those skilled in the art will appreciate that the device can likewise be structured such that the inner sheath is permanently affixed in the device. In this event, the device can simply be discarded following use.

During manual operation of device 10 shown in FIGS. 1-4, the operator pulls trigger 36 in the linear direction shown. As discussed, this action drives, or translates, the linear motion of the trigger pull to rotary movement of hub 50, thereby causing rotation of inner sheath 14. The remaining features of the translation mechanism not described herein are conventional, and need not be further explained or illustrated to enable one skilled in the art to utilize the mechanism for the purposes described.

Rack and gear structures are well known in the art, and the specific structure described and shown herein is not intended to represent the only way that such translation can be accomplished. Those skilled in the art will appreciate that there are numerous other ways in which a manual device can be structured such that an action generated by an operator, such as the trigger pull described herein, may result in rotary motion. All such techniques within the knowledge of one skilled in the art are considered within the scope of the invention.

Figure 5:
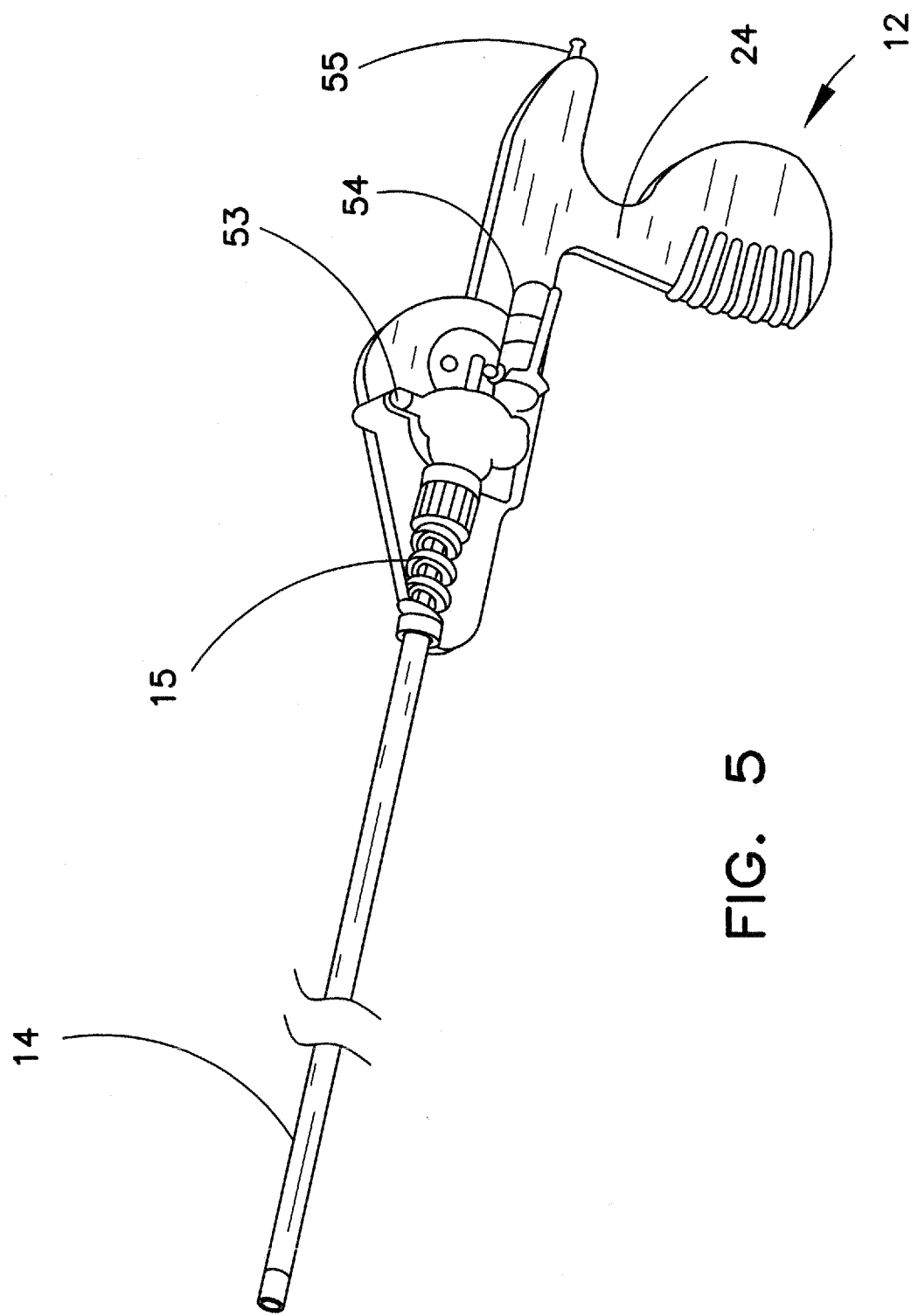
FIG. 5 is a view of the reverse side of a handle and an inner sheath of a lead extraction device including a power supply.

FIG. 5 illustrates another example of the lead extraction device. In this example, the rack and gear structure, as well as the trigger of FIGS. 1-4, have been eliminated. These features have been replaced with a power source, such as drive motor 54. The power source may comprise any conventional source suitable for driving the rotation of the hub, such as a source for generating electrical, battery or pneumatic power. A suitable actuator, such as button 55, may be provided to selectively activate, and deactivate, drive motor 54. Upon actuation, the drive motor operates in well known fashion to cause inner sheath 14 to rotate.

Although the translational mechanism and trigger have been removed from the embodiment shown in FIG. 5, this need not be the case. Rather, device 10 can be provided with both a manual operation (such as via trigger 36 and translation mechanism 34) and a powered operation (such as via drive motor 54). In this case an operator can selectively utilize either, or both, of these features during a particular lead extraction procedure.

Respective inner and outer sheaths 14, 16 may be formed from conventional biocompatible materials well known for such purposes in the medical arts. Polymeric materials such as polypropylene, polyurethane, polyethylene, nylon, PTFE, and the like, are believed to be particularly appropriate. As stated above, extraction devices often comprise an inner sheath 14 having a tip engaged at the distal end of the inner sheath, and a telescoping outer sheath 16. Suitable tips for the inner sheath are further described, e.g., in the aforementioned incorporated-by-reference patent documents listed above.

The inner and/or outer sheath can be reinforced with a coil or with a braided material if desired. Such reinforcements are well known in the medical arts, and are typically formed from a metal or metal alloy, or from a composite material. Non-limiting examples of suitable reinforced sheaths are disclosed in, e.g., U.S. Pat. No. 5,380,304 and U.S. Patent Publ. No. 2001/0034514, incorporated by reference herein. The sheaths described hereinabove are exemplary, and those skilled in the art will appreciate that other sheaths known to be suitable for use in the medical arts may be substituted, such substitutions being within the scope of the invention. Those skilled in the art are readily capable of optimizing the properties of a medical sheath, e.g., the hardness, flexibility, length, etc., of the sheath, in view of the intended use of the sheath.

Generally speaking, at least an inner sheath for use in a device for removing an implanted elongated structure, such as a cardiac lead, should have a length and flexibility such that the sheath is capable of advancing through enough of the body vessel to at least partially free the cardiac lead from encapsulating endothelial growth. For best results, this sheath should be structured such that torque can be transmitted by the operator from the proximal end of the sheath to the distal tip. In this manner, the operator need merely insert the sheath into the vessel, and may thereafter direct, or torque, the sheath to the desired site to enable the inner sheath tip to core or otherwise non-cuttingly disrupt the growth encapsulating the lead.

As stated in the incorporated-by-reference documents, an inner sheath assembly 13 can include an inner sheath 14 and a tip 18 secured to the distal end of the inner sheath. Tips suitable for use herein on the inner sheath may be fabricated by known techniques, such as machining and metal injection molding, from materials having sufficient strength and rigidity to advance through or otherwise disrupt obstructions encountered during removal of the elongated implanted structure. Metals and metal alloys, such as stainless steel, nitinol and titanium, are particularly preferred tip materials. Those skilled in the art will appreciate that other compatible materials may be used in place of metal or metal alloys. For example, the tip may alternatively be formed from a fiber-reinforced polymer, such as fiber-reinforced polypropylene. Non-limiting examples of suitable fiber reinforcements include glass and carbon fibers. In one example, the tip may be formed of a polymer, such as polypropylene, and may be molded or bonded onto the end of a sheath. When the tip is formed from a polymer, the sheath may be formed from a polymer that is compatible with the polymer of the tip material. In most cases, it is preferred to provide a tip formed of a composition having greater strength and/or hardness than the sheath, so that the tip is better able to core or otherwise disrupt the endothelial growth from around the implanted device.

Figure 6:
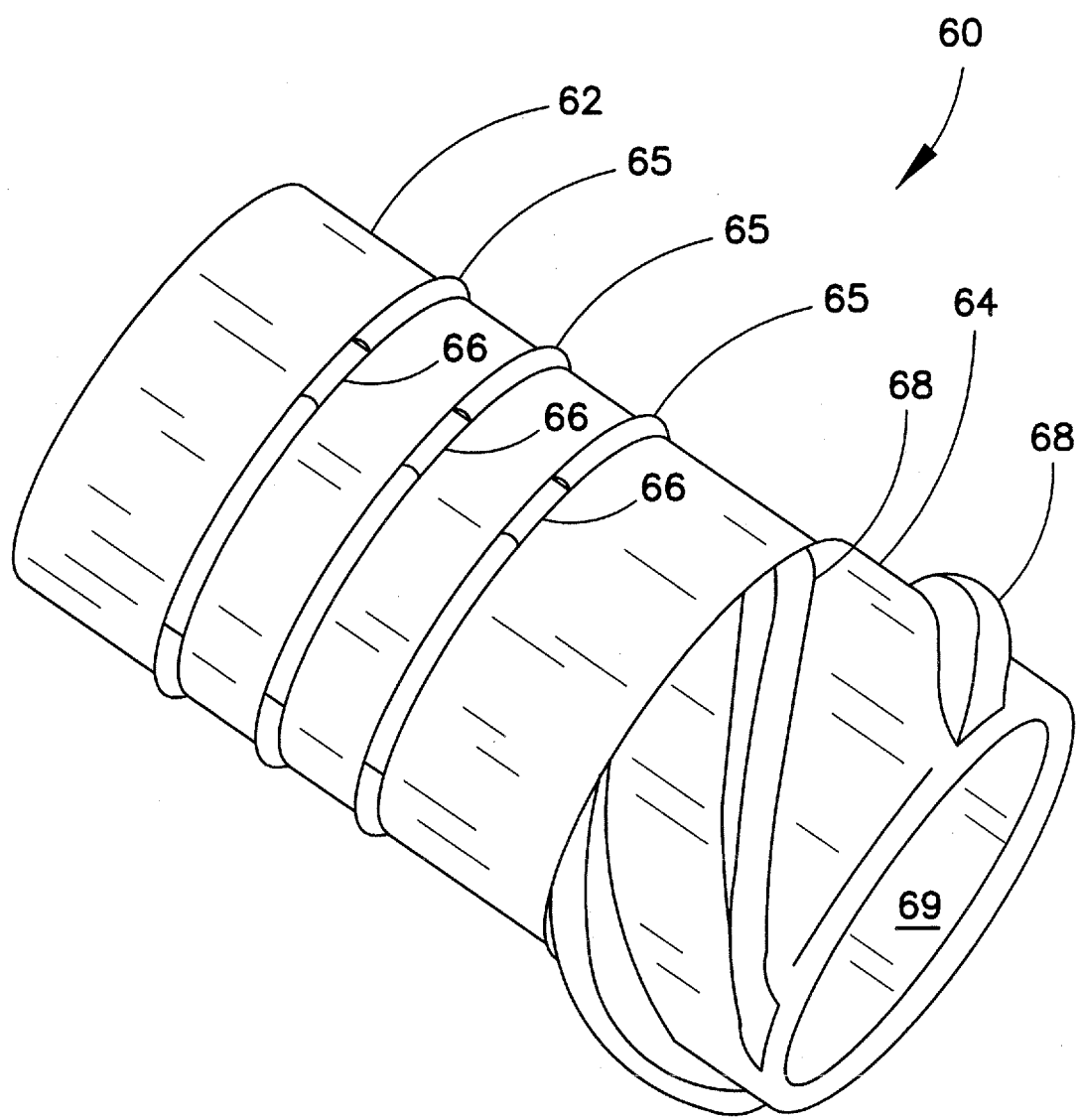
FIG. 6 is one example of a distal tip for an inner sheath known in the art.
Figure 7:
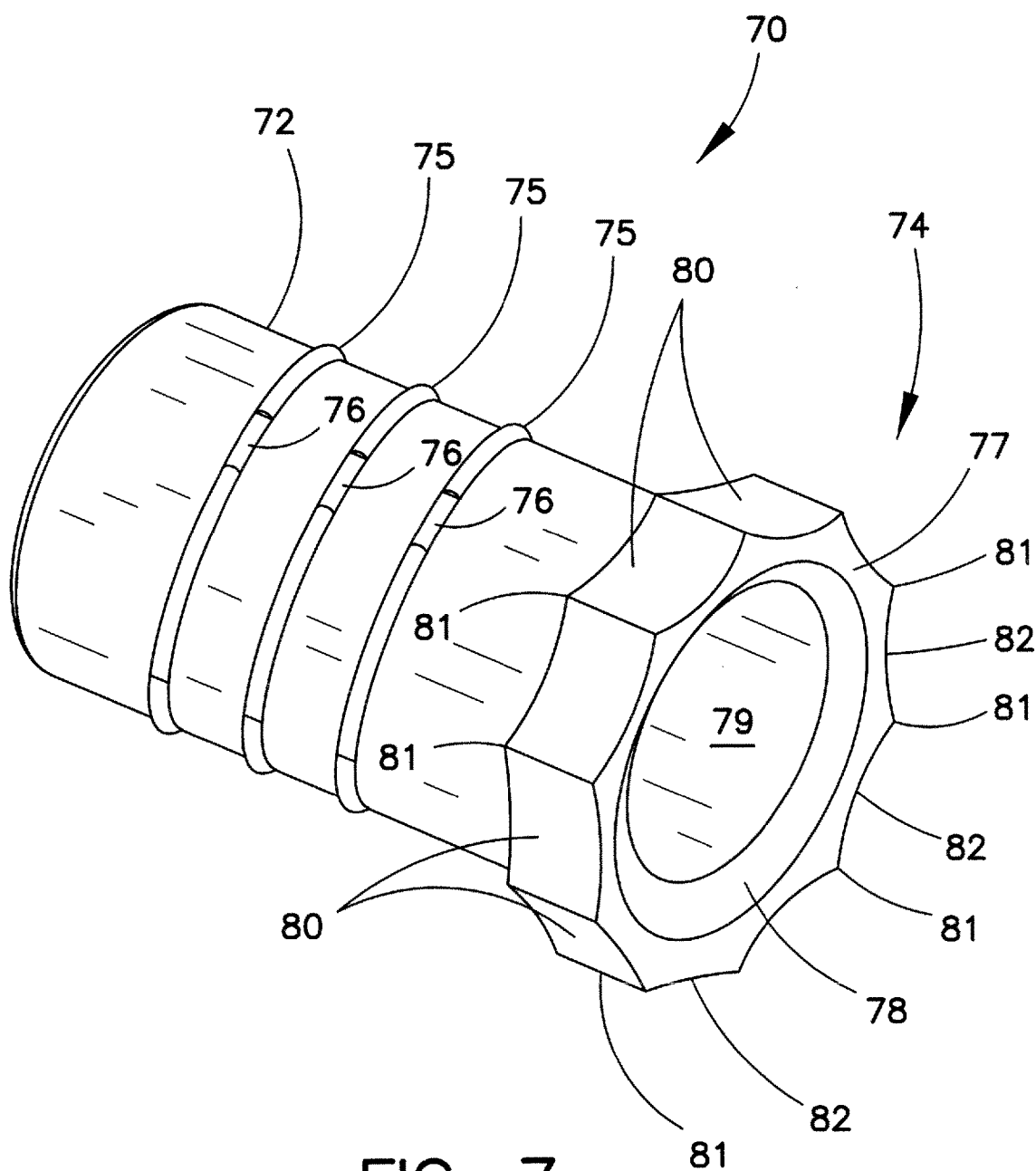
FIG. 7 is another example of a distal tip for an inner sheath known in the art.

FIGS. 6 and 7 illustrate examples of distal tips for an inner sheath assembly known in the art. Distal tip 60, as illustrated in FIG. 6, is similar to a tip disclosed in the incorporated-by reference U.S. Patent Publ. No. 2006/0253179. This tip includes a smaller diameter proximal portion 62, a larger diameter distal portion 64, and a passageway 69 extending axially through the tip. The tip may be affixed to the distal end of the sheath, such as inner sheath 14, by affixing smaller diameter proximal tip portion 62 to the inner surface at the distal end of a sheath 14. In the example shown in FIG. 6, smaller diameter portion 62 is provided with a plurality of rings 65 along its outer surface. If desired, rings 65 may be aligned in order of increasing width of the ring body in the direction of the distal tip portion. Providing rings having a smaller width in the proximal direction minimizes the stresses in the sheath at the area of joinder of the sheath and the tip. At the area of joinder with the sheath, stresses resulting from tension, torsion, and bending tend to be the highest. If desired, rings 65 may be provided with one or more cut-outs 66. Cut-outs 66 serve to hinder rotation of the tip when the proximal tip portion is positioned inside the distal portion of the sheath.

In this example, tip 60 includes a series of radially outwardly directed disrupter elements, such as helices 68, on the outer surface of larger diameter distal tip portion 64. Tips having such outwardly projecting elements are generally referred to as disrupter tips, since the action of these tips primarily "disrupts", rather than cores or cuts, the obstructing tissue from the vessel wall. By gently disrupting the obstruction, rather than cutting or coring it, the tips have a reduced propensity to cut a lead or breach a vessel wall. While disrupting the tissue, the disrupter elements urge the tissue to move in a direction which may be different from the direction of motion of the disrupter element.

Distal tip 70, as illustrated in FIG. 7, is similar to a tip disclosed in the incorporated-by reference U.S. Patent Publ. No. 2012/0323252. Tip 70 includes a smaller diameter proximal portion 72, a larger diameter distal portion 74, and a passageway 79 extending axially through the tip. This tip may be affixed to the distal end of the inner sheath in the same manner as tip 60. In this example, smaller diameter portion 72 has a plurality of rings 75 along its outer surface, which rings may have cut-outs 76. Tip 70 may have a substantially flat leading face 77, and a radiused portion 78 leading into the passageway. The tip body distal portion 74 includes a plurality of sides 80 extending circumferentially therearound. The sides have respective ends 81, and an inwardly directed radiused portion 82 between the ends.

The tips shown in FIGS. 6 and 7 are examples of known tips affixed to an inner sheath for an extraction device. Other suitable tip structures are also well known in the art. In addition to the joinder rings shown in the tips of FIGS. 6 and 7, a tip may be joined to the distal end of inner sheath 14 by other well-known means, e.g., bonding, adhering, or other chemical or mechanical affixation means to ensure that the tip will not disengage from the sheath under conditions encountered during normal use.

Typically, in prior art extraction devices the outer sheath has a minimal role for freeing an implanted device. The cutting and/or disrupting of the device from the encumbrances is generally accomplished by the rotating action of the inner sheath and tip. In such instances, the outer sheath essentially functions as a conduit to facilitate advancement of the inner sheath, and does not provide an appreciable disrupting and/or cutting action to the device. In many cases, this extraction process works well, and the cardiac lead or other implanted device may be freed from the encumbrances by action of the inner tipped sheath, and thereby removed from the vessel. However, there remain particularly troublesome instances in which the inner sheath and tip are not readily able to free the lead from the encumbrances.

Figure 8:
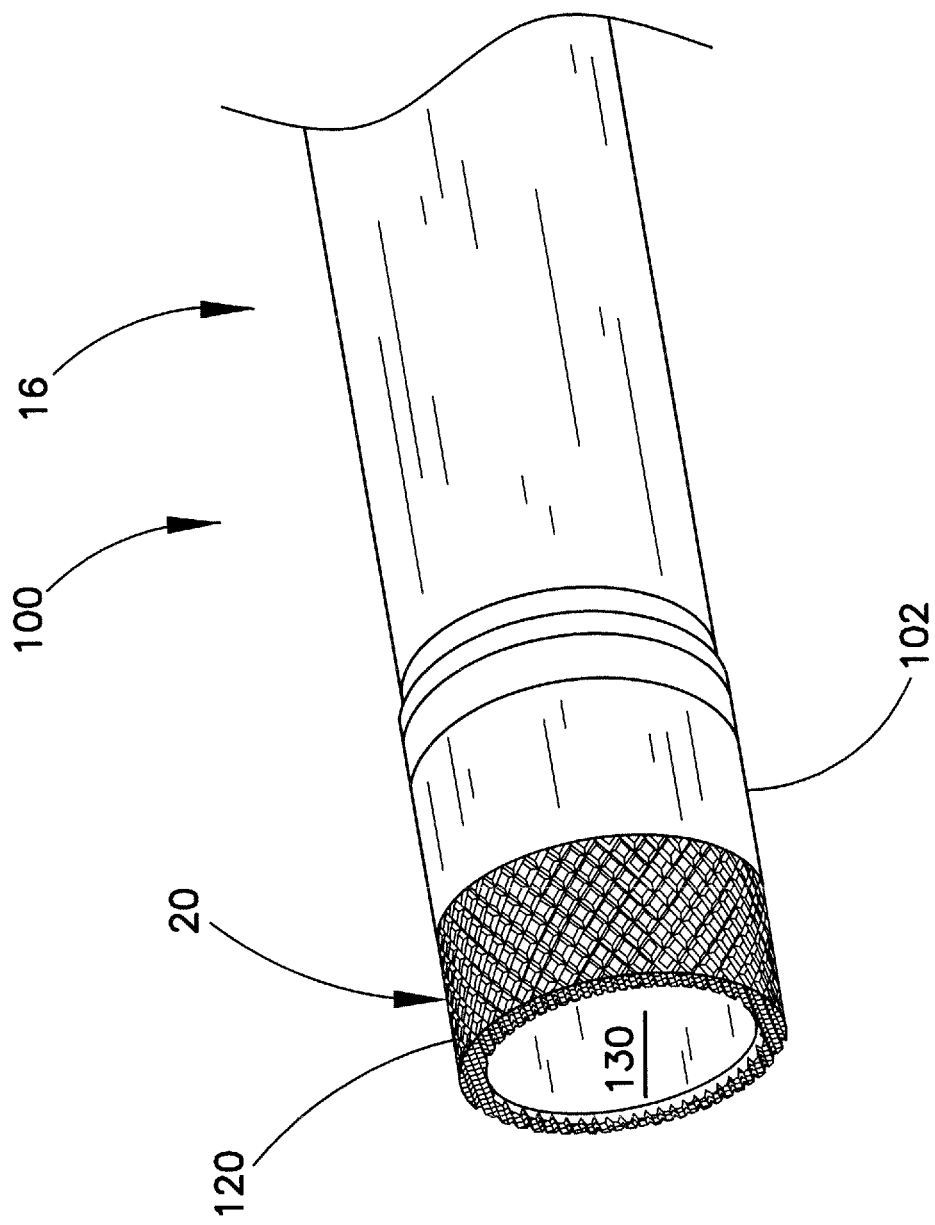
FIG. 8 is a perspective view of the distal portion of one example of an outer sheath assembly.
Figure 9:
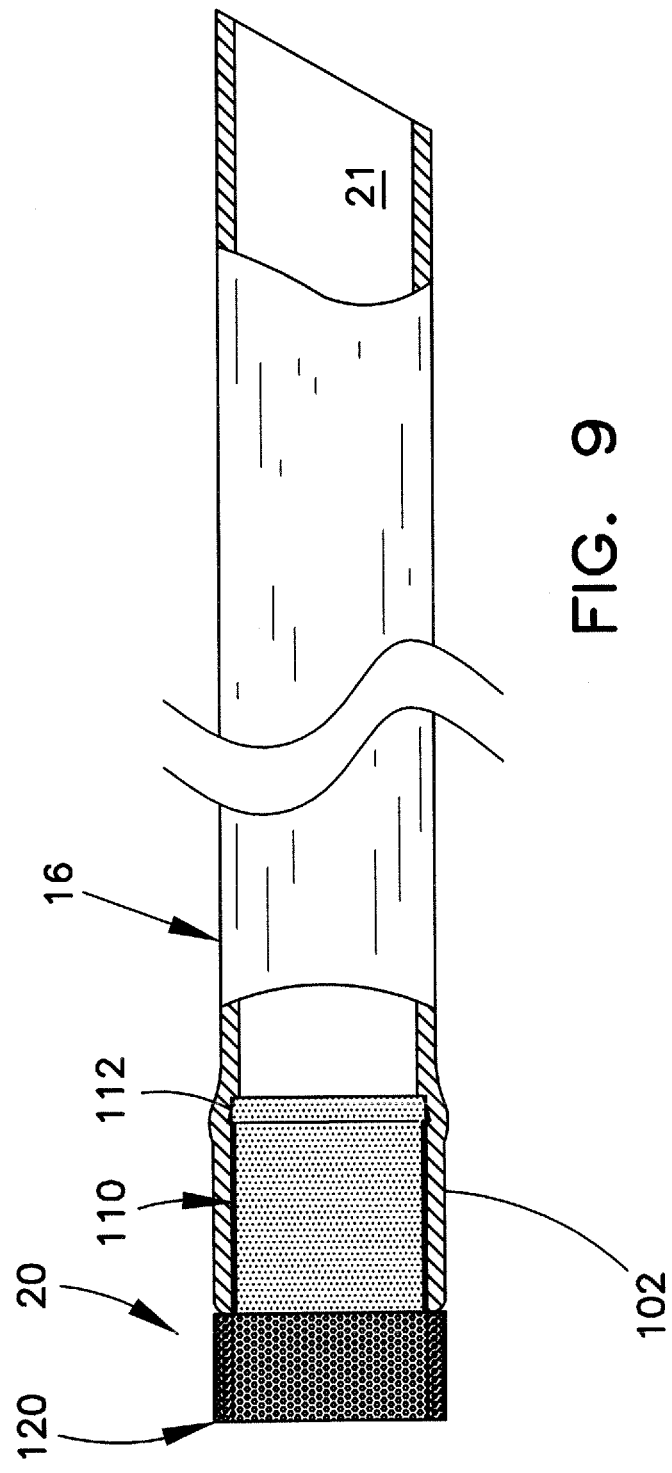
FIG. 9 is a longitudinal view of the outer sheath assembly of FIG. 8, partially in section.
Figure 10:
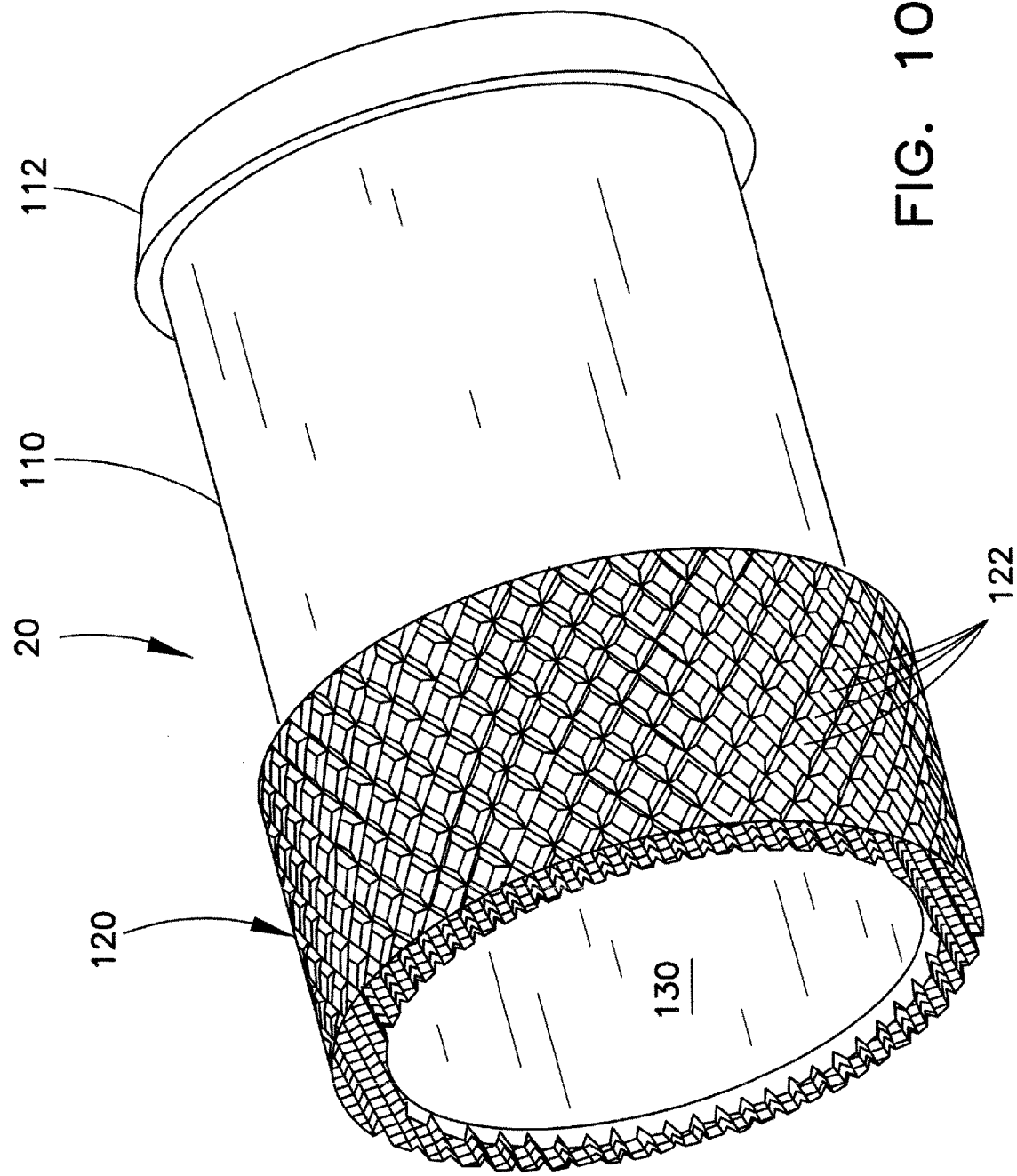
FIG. 10 is an enlarged perspective view of one example of a tip for the outer sheath assembly of FIG. 8.

FIG. 8 illustrates a perspective view of the distal end portion of an outer sheath assembly 100 of a type that may be utilized in an extraction device, such as lead extraction device 10. Assembly 100 includes outer sheath 16 and tip 20. FIG. 9 illustrates a longitudinal view of outer sheath assembly 100, partially in section. FIG. 10 illustrates an enlarged perspective view of one example of tip 20.

In the example shown, tip 20 has a smaller diameter proximal portion 110 and a larger diameter distal portion 120. A passageway 130 extends through tip 20, such that when the tip is affixed to the distal end of outer sheath 16, tip passageway 130 is aligned with sheath passageway 21 to enable passage therethrough of the implanted structure, e.g., the cardiac lead.

Smaller diameter proximal portion 110 of the tip 20 may be received in, and engaged with, the inner surface at the distal end 102 of sheath 16. The proximal end of smaller diameter portion 110 may include a shaped structure, such as truncated conical portion 112, for enhancing the engagement with the sheath inner surface. This arrangement is shown in FIGS. 9 and 10. This is merely one example of a suitable engagement mechanism between sheath 16 and tip 20. Those skilled in the art will appreciate that other known engagement mechanisms, such as the rings 66, 76, shown in FIGS. 6 and 7 may be substituted. Similarly, the proximal end of tip 20 can be provided with one or more anchors, barbs, and/or other attachment mechanisms positioned along the proximal length of the tip, which attachment mechanisms are configured to fixedly engage the inner surface of the sheath. In most such arrangements, the tip and the sheath will be at least substantially immovable relative to each other. As still other alternatives, the proximal end of tip 20 can be adhered to the inner surface of sheath 16 by adhesion, bonding, and/or other means well known in the art.

Although preferred, it is not required that tip 20 include a smaller diameter portion for engagement with an inner surface of sheath 16. Rather, for example, this arrangement can be reversed, such that a proximal end of the tip can be received over a smaller diameter distal tip portion of the sheath. As a still further alternative, sheath 16 and tip 20 can be provided with other complementary structure for joinder, such as mutually tapered ends. Regardless of the engagement means employed, it is generally preferred that the outer diameter of the sheath will be at least substantially the same as the outer diameter of the exposed portion of the tip (e.g., larger diameter portion 120 in the example of FIG. 10), such that a substantially constant diameter outer surface is provided along the distal portion of the sheath assembly 100. Although this arrangement is preferred, it is not critical, as those skilled in the art will appreciate that other diameters may be suitable for a particular application.

The tip will now be described with reference to the distal tip geometry shown in FIG. 10. Those skilled in the art will appreciate that this illustrated example represents only one possible tip configuration and distal tip geometry, and that other configurations may be substituted for a particular application within the scope of the invention.

In the example shown, distal tip portion 120 is provided with a shaped outer surface, such as the knurled-type surface shown in the figures. As known in the art, a knurled surface is one having a plurality of raised surfaces disposed along the circumference of the distal tip portion, such as the generally-diamond-shaped surfaces 122 shown in the figure.

Providing a tip having raised surfaces helps to steady or stabilize the adjacent tissue upon contact of the raised surfaces with the inner wall of the vessel. As a result, the tissue along the inner wall of the vessel at least substantially remains in place, and thereby, does not rotate along with the tip of the rotatable inner sheath. This allows for more efficient disrupting, or coring, of the encumbrance by the inner sheath tip as the device advances along the implanted lead. In one preferred form, the elements disposed along the outer surface of tip portion 120 are configured in a manner to facilitate a non-cutting engagement with the obstruction. In this manner, advancement of the outer sheath over the implanted structure and into the obstruction causes the elements to push aside and separate the obstruction from the implanted structure without a forward cutting action.

One example of the knurled outer surface of sheath distal tip portion 120 is shown in FIG. 10. In this example, the raised portions comprise diamonds 122 arranged in the pattern as shown. In theory, any number and pattern of raised elements can be provided along the outer surface of distal tip portion 120. In this example, diamonds 122 can be arranged in substantially helical rows along the outer surface, wherein each row has, e.g., about ten diamonds. The artisan will also recognize that the number, and pattern, of the raised diamonds as shown in the figures is merely one example, and that other numbers, and patterns, may be substituted as may be advantageous for a particular application. In fact, it is not required that a distinct pattern of diamonds be provided, and in many cases a random distribution of such knurled-type structures along the outer surface of the tip will be suitable.

In one preferred form, distal tip portion 120 may have an outer diameter of about 9 French. Those skilled in the art will appreciate, however, that distal tip portion 120 can have any suitable outer diameter for the particular task at hand, such as about 9, 11, 13, 15, etc., French. Thus, for example, the outer diameter can be varied depending upon the inner diameter of the vessel into which the sheath assembly is to be inserted, and in view of the diameter of the implanted structure which is intended for removal. In one non-limiting example, the outer diameter may be 9 French, and the length of the tip 20 can range between about 7.7 and 9.6 mm. The length of large diameter distal portion 120 may be between about 3.0 and 3.2 mm, and the length of the smaller diameter proximal portion may be between about 4.7 and 6.4 mm. The skilled artisan will appreciate that these lengths, as well as the respective inner and outer diameters of the tip and sheath may be modified as desired for a particular application.

Although the example described and shown above includes a knurled-type surface comprising the geometric pattern of diamonds, the use of the diamonds is only one example. Those skilled in the art will appreciate that raised elements of virtually any geometric shape, or combination of shapes, may be utilized, as long as the raised portions are suitable for steadying and/or stabilizing the tissue upon contact, as described. Another advantage of the use of the knurled elements as described, and particularly when present in a distinct pattern along the tip, is the enhanced visibility that may result under medical imaging techniques (e.g., fluoroscopy) in appropriate instances.

The tip embodiment as shown and described in FIGS. 9 and 10 does not have a leading (i.e., axial) disrupting, coring, and/or cutting element. Rather, the tip has raised surfaces that project radially from the distal tip surface in a manner to steady or stabilize the adjacent tissue upon contact of the raised surfaces with the inner wall of the vessel, as previously described. In some examples, however, it may be desired to provide the tip of the outer sheath assembly with disrupting, coring and/or cutting structure. In these examples, it is desired to provide assistance to the inner sheath assembly in advancing over the implanted lead along the vessel.

FIG. 11 illustrates one example of an outer sheath assembly 140 having a distal tip as described. In this example, the proximal end of tip 142 may be engaged with the distal end of sheath 16 by any of the attachment modes described above. The leading end 144 of tip 142 is structured in a manner to assist the inner sheath assembly as device 10 advances through the obstruction. In this example, leading end 144 is provided with one or more scallops 146 disposed along the circumference of the leading end. Scallops 146 allow distal tip 142 to advance into the obstruction, and when rotated, act in the nature of a low profile disrupting, coring, or cutting tip. Although not required in all instances, in most cases tip 142 will provide less aggressive action against the encumbrances than the disrupting, coring and/or cutting tip of the inner sheath assembly. However, tip 142 may provide enough of a boost in disrupting, etc., to enable the extraction device 10 to advance through a particularly troublesome obstruction.

As an alternative to scallops, the leading end of tip 142 can be provided with alternative structure, such as the structures shown in FIGS. 21-26 of the incorporated-by-reference U.S. Patent Publ. No. 2006/0253179. Unlike the tips shown in the incorporated-by-reference publication, the tips for the outer sheath assembly disclosed herein need not always be provided with a leading face as aggressive as the leading face disclosed therein. Rather, the tips on the outer assembly are generally provided to have a secondary role to the inner sheath assembly in enabling device 10 to advance through an obstruction, and therefore, need not include more aggressive structure of a type that may be provided on the tip of the inner sheath assembly. As a further alternative, such tips of the outer sheath assembly may be provided with any combinations of raised elements, such as the knurled elements shown and described, and the leading end structure as described (e.g., scallops of FIG. 11), and/or any of the configurations of the tips of FIGS. 6 and 7.

If desired, selected portions of the lead extraction device 10 described herein, such as the tip portion of the inner and/or outer sheath assembly, can be provided with imaging means for use with, e.g., x-ray, MRI, or ultrasound. Such means are well known in the art, and may include, for example, the incorporation of a radiopaque and/or echogenic feature into a selected portion of the tip. Increased visibility of the tip may be beneficial, as it provides the operator with the ability to determine the location of the tip at a particular point in time. In addition, it provides the operator with the ability to track the position and orientation of the tip with reference to the lead body.

Those skilled in that art will appreciate that the foregoing detailed description should be regarded as illustrative rather than limiting, and that it should be understood that it is the following claims, including all equivalents, that are intended to define the spirit and scope of this invention.

What is claimed is:

1. A device for extracting an elongated implanted structure from an obstruction within a vessel of a patient, comprising:
    an inner sheath assembly comprising an inner sheath and an inner tip, the inner sheath having a distal end and having a passageway extending therethrough, the inner sheath being sufficiently flexible to track over the implanted structure within the vessel; the inner tip having a proximal portion, a distal portion having an outer surface, and a passageway extending therethrough, the proximal portion of the inner tip engaged with the inner sheath distal end such that the respective passageways are aligned to receive the implanted structure therein, the distal portion of the inner tip having an outer surface including a plurality of outwardly directed disrupter elements circumferentially disposed therealong, the plurality of disrupter elements each having a circumferentially oriented surface that is configured to laterally engage tissue upon rotation of the inner sheath assembly and facilitate disruption of the implanted structure from the obstruction; and
    an outer sheath assembly comprising an outer sheath and an outer tip, the outer sheath having a distal end, an outer diameter, and a passageway extending therethrough, the outer sheath being sufficiently flexible to track over the inner sheath assembly; the outer tip having a proximal portion, a distal portion, and a passageway extending therethrough, the outer tip proximal portion engaged with the outer sheath distal end such that the respective passageways are aligned to receive the inner sheath assembly therein, the outer tip distal portion having a plurality of outwardly directed helical stabilizing elements circumferentially disposed therealong, the plurality of helical stabilizing elements being configured to engage and stabilize the vessel during an advancement of the inner sheath assembly through the vessel,
    wherein the plurality of disruptor elements and the plurality of helical stabilizing elements each comprise a different shape; and
    wherein the outer sheath assembly is axially and rotationally movable relative to the inner sheath assembly.

2. The device of claim 1, wherein the plurality of disruptor elements comprises a plurality of longitudinally oriented edges disposed parallel to a central longitudinal axis of said inner tip, and wherein an inwardly directed radiused portion extends between each pair of adjacent edges.

3. The device of claim 1, wherein the plurality of disruptor elements comprises a plurality of helically oriented edges disposed along the inner tip distal portion.

4. The device of claim 1, wherein the plurality of helical stabilizing elements comprises a knurled surface disposed along the outer surface of the outer tip distal portion.

5. The device of claim 1, wherein the plurality of helical stabilizing elements comprises a plurality of substantially helical rows of raised elements disposed along the outer surface of the outer tip distal portion.

6. The device of claim 1, wherein the proximal portion of the outer tip has a smaller outer diameter, and the distal portion of the outer tip has a larger outer diameter, said smaller outer diameter proximal portion sized and configured for engagement with an inner surface of the outer sheath distal end.

7. The device of claim 1, wherein the distal portion of the outer tip has a distal leading end, the distal leading end configured for disrupting the obstruction from said implanted structure upon an advancement of said outer sheath assembly within said vessel.

8. The device of claim 7, wherein the distal leading end of the outer tip comprises a distal face having one or more scallops for disrupting the obstruction.

9. The device of claim 1, wherein the outer tip distal portion comprises a first set of surface features and the inner tip distal portion comprises a second set of surface features, the second set of surface features being dissimilar to the first set of surface features.

10. The device of claim 1, wherein the outer tip of the outer sheath assembly comprises at least one of a radiopaque and an echogenic element.

11. The device of claim 1, further comprising a drive member operationally engaged with the inner sheath assembly for driving at least one of rotational and axial movement of said inner sheath assembly.

12. The device of claim 1, wherein the plurality of disruptor elements of inner tip distal portion project radially outwardly beyond an outer surface of the inner sheath so as to inhibit the outer sheath assembly from axially moving in a distal direction beyond the distal end of the inner sheath.

13. A device for extracting an elongated implanted structure from an obstruction within a body vessel of a patient, comprising:
    an inner sheath assembly comprising an elongated inner sheath and an inner tip positioned at a distal end of the inner sheath, each of the inner sheath and inner tip having a passageway therethrough for receiving the implanted structure therein, a distal portion of the inner tip comprising a plurality of outwardly directed disrupter elements circumferentially disposed along an outer surface thereof, the plurality of outwardly directed disrupter elements configured for separating the implanted structure from the body vessel;
    an outer sheath assembly comprising an elongated outer sheath and an outer tip affixed at a distal end of the outer sheath, each of the outer sheath and outer tip having a passageway therethrough for receiving the inner sheath assembly, a distal portion of the outer tip including a plurality of individual and separate raised stabilizing elements circumferentially disposed along an outer surface thereof, the plurality of raised stabilizing elements configured for stabilizing the body vessel during an advancement of the inner sheath assembly relative to the outer sheath assembly and through the body vessel; and a handle configured for engagement with a proximal end of the elongated inner sheath, the handle including an actuator and a drive mechanism responsive to the actuator, the drive mechanism operable for selectively translating input of the actuator into at least one of rotational and axial movement of the inner sheath assembly in the vessel, wherein the plurality of outwardly directed disruptor elements comprises a plurality of helically or longitudinally oriented edges disposed along the inner tip distal portion, and wherein the plurality of outwardly directed disrupter elements and the plurality of raised stabilizing elements and comprise dissimilar shaped surface features.

14. The device of claim 13, wherein the plurality of raised stabilizing elements comprises a knurled surface disposed along said outer surface.

15. The device of claim 14, wherein the knurled surface comprises a plurality of surface features disposed in substantially helical rows.

16. The device of claim 13, wherein the outer tip of the outer sheath assembly has a distal leading end configured for disrupting the obstruction from the implanted structure upon an advancement of the outer sheath assembly within the body vessel.

17. The device of claim 13, wherein the plurality of outwardly directed disruptor elements comprises the plurality of longitudinally oriented edges disposed parallel to a central longitudinal axis of said inner tip, and wherein an inwardly directed radiused portion extends between each pair of adjacent edges.

18. The device of claim 13, wherein the plurality of outwardly directed disruptor elements comprises the plurality of helically oriented edges disposed along the inner tip distal portion.

19. The device of claim 13, wherein the outer tip of the outer sheath assembly comprises at least one of a radiopaque and an echogenic element.

20. A device for extracting an elongated implanted structure from an obstruction within a vessel of a patient, comprising:

an inner sheath assembly comprising an inner sheath and an inner tip, the inner sheath having a distal end and having a passageway extending therethrough, the sheath being sufficiently flexible to track over the implanted structure within the vessel; the inner tip having a proximal portion, a distal portion having an outer surface, and a passageway extending therethrough, the proximal portion of the inner tip engaged with the inner sheath distal end such that the respective passageways are aligned to receive the implanted structure therein, the distal portion of the inner tip comprising a scalloped outer surface disposed circumferentially thereabout, the scalloped outer surface comprising a plurality of outwardly projecting unitary edges disposed parallel to a central longitudinal axis of said inner tip, and an inwardly directed radiused portion extending between each pair of adjacent unitary edges, the scalloped outer surface being configured to facilitate disruption of the implanted structure from the obstruction; and an outer sheath assembly comprising an outer sheath and an outer tip, the outer sheath having a distal end, an outer diameter, and a passageway extending therethrough, the outer sheath being sufficiently flexible to track over the inner sheath assembly; the outer tip having a proximal portion, a distal portion, and a passageway extending therethrough, the outer tip proximal portion engaged with the outer sheath distal end such that the respective passageways are aligned to receive the inner sheath assembly therein, the outer tip distal portion comprising a knurled outer surface having a plurality of individual spaced apart projections disposed longitudinally and circumferentially therabout, said knurled outer surface being configured for stabilizing said body vessel during advancement of the inner sheath assembly relative to the outer sheath assembly, wherein the outer sheath assembly is axially and rotationally movable relative to the inner sheath assembly.

* * * * *